(12) United States Patent
Gabel et al.

(10) Patent No.: US 7,473,798 B2
(45) Date of Patent: Jan. 6, 2009

(54) DERIVATIVES OF UNSATURATED, CYCLIC ORGANIC ACIDS

(75) Inventors: Richard A. Gabel, Louisville, CO (US); Michael D. Groaning, Boulder, CO (US); David A. Johnston, Louisville, CO (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/645,096

(22) Filed: Dec. 22, 2006

(65) Prior Publication Data

US 2007/0197807 A1 Aug. 23, 2007

Related U.S. Application Data

(60) Provisional application No. 60/754,740, filed on Dec. 28, 2005.

(51) Int. Cl.
C07C 67/08 (2006.01)
C07C 69/757 (2006.01)
C07C 309/66 (2006.01)

(52) U.S. Cl. .................................................. 560/128

(58) Field of Classification Search ........................ None
See application file for complete search history.

(56) References Cited

U.S. PATENT DOCUMENTS

| | | | |
|---|---|---|---|
| 5,399,778 A | 3/1995 | Steffen et al. |
| 5,886,213 A | 3/1999 | Kent et al. |
| 6,303,764 B1 | 10/2001 | Srivastava et al. |
| 6,420,552 B1 | 7/2002 | Srivastava et al. |
| 6,590,119 B2 | 7/2003 | Ferro et al. |
| 2004/0053999 A1 | 3/2004 | Bischofberger et al. |

FOREIGN PATENT DOCUMENTS

| | | |
|---|---|---|
| EP | 1112999 | 7/2001 |
| EP | 1146036 | 10/2001 |
| WO | WO 96/26933 | 9/1996 |
| WO | WO 98/07685 | 2/1998 |
| WO | WO 99/14185 | 3/1999 |
| WO | WO 99/55664 | 11/1999 |

OTHER PUBLICATIONS

Kim, C.U. et al., "Structure-Activity Relationship Studies of Novel Carbocyclic Influenza Neuraminidase Inhibitors," J. Med. Chem,, 41, pp. 2451-2460, 1998.

Kim, C.U. et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," J. Am. Chem. Soc., 119, pp. 681-690, 1997.

Federspiel et al., "Industrial Synthesis of the Key Precursor in the Synthesis of the Anti-Influenza Drug Oseltamivir Phosphate (Ro 64-0796/002, GS-4104-02): Ethyl (3R,4S,5S)-4,5-epoxy-3-(1-ethyl-propoxy)-cyclohex-1-ene-1-carboxylate," Organic Process Research & Development, vol. 3, No. 4, pp. 266-274, 1999.

Conia, J.M. et al., "Sur la preparation de cyclopenténones par action de l'acide polyphosphorique sur les esters d'acides α-éthyléniques," Bulletin de la Société Chimique de France, pp. 2981-2991, 1970.

March, J., "Aliphatic Nucleophilic Substitution," Advanced Organic Chemistry, 484-486, 2001.

Armesto, N. et al., Efficient synthesis of (-)-methyl 3-*epi*-shikimate and methyl 3-*epi*-quinate by one-pot selective protection of *trans*-1,2-diols, Tetrahedron Letters, 41, pp. 8759-8762, 2000.

*Primary Examiner*—James O. Wilson
*Assistant Examiner*—Yevegeny Valenrod
(74) *Attorney, Agent, or Firm*—Brian L. Huckwalter

(57) ABSTRACT

The present invention relates to technology for preparing derivatives of unsaturated, cyclic, organic acids and salts, thereof. Shikimic acid is an example of such an acid. More particularly, the present invention relates to preparing derivatives of these acids or salts thereof that are esterified, ketalized, functionalized with a leaving group, and/or provided with epoxide functionality. Preferred aspects may be used in the synthesis of Oseltamivir Phosphate starting from shikimic acid.

14 Claims, No Drawings

DERIVATIVES OF UNSATURATED, CYCLIC ORGANIC ACIDS

PRIORITY CLAIM

The present non-provisional patent Application claims priority under 35 USC §119(e) from United States Provisional Patent Application having Ser. No. 60/754,740, filed on Dec. 28, 2005, by Gabel et al. and titled DERIVATIVES OF UNSATURATED, CYCLIC ORGANIC ACIDS, wherein the entirety of said provisional patent application is incorporated herein by reference.

FIELD OF THE INVENTION

The present invention relates to technology for preparing derivatives of unsaturated, cyclic, organic acids and salts, thereof. Shikimic acid is an example of such an acid. More particularly, the present invention relates to preparing derivatives of these acids or salts thereof that are esterified, mesylated, ketalized, and/or provided with epoxide functionality. Preferred aspects may be used in the synthesis of Oseltamivir Phosphate starting from shikimic acid.

BACKGROUND OF THE INVENTION

Oseltamivir Phosphate, widely known under the trade designation TAMIFLU, is targeted for use as an antiviral compound to prevent and/or treat influenza infections. Oseltamivir Phosphate has been described in C. U. Kim et al., *J. Med. Chem.* 1998, 41, 2451; C. U. Kim et al., *J. Am. Chem. Soc.* 1997, 119,681; and M. Federspiel et al., *Organic Process Research & Development* 1999, 3, 266-274, the entireties of which are incorporated herein by reference in their respective entireties for all purposes.

Oseltamivir Phosphate has the formula

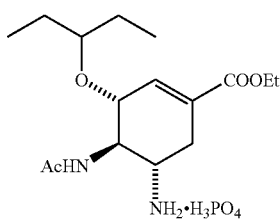

and is the prodrug of the potent neuraminidase inhibitor having the formula:

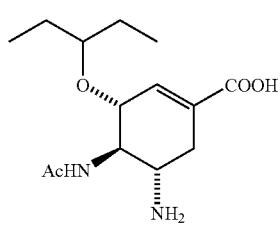

The literature describes preparing Oseltamivir Phosphate in multistep syntheses starting from either quinic acid:

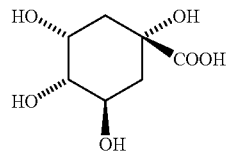

or shikimic acid:

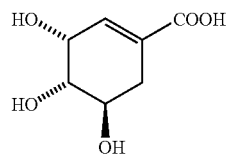

See M. Federspiel et al., *Organic Process Research & Development* 1999, 3, 266-274.

Synthesis from quinic acid generally was proposed first. The synthesis via quinic acid was satisfactory for the production of kilogram quantities of Oseltamivir Phosphate, but as the demand for Oseltamivir Phosphate increased and continues to increase, better synthesis techniques more suitable for larger scale production are desired. Syntheses of Oseltamivir Phosphate starting from shikimic acid were developed as a result of this desire. Shikimic acid-based syntheses offer great potential due to the fact that the desired carbon-carbon double bond is already present, whereas the double bond has to be created when starting from quinic acid. Having a starting material that already incorporates the desired double bond bypasses the regioselective dehydration associated with developing this functionality in the quinic acid routes.

The article by M. Federspiel cited herein describes two potential synthesis routes of Oseltamivir Phosphate starting from shikimic acid. One synthesis involves the direct ketalization of a shikimic acid ester. The other proceeds via an acetonide intermediate. Even though the acetonide route involves more steps and more isolations, the authors strongly prefer the acetonide route over the direct ketalization route. The authors discarded the direct ketalization route as impractical because the intermediates (the ketalized shikimic acid ester and the mesylated, ketalized shikimic acid ester) are oils and had to be carried through in crude form until the step in which the crystalline epoxide could be purified efficiently.

In the meantime, the demand for Oseltamivir Phosphate continues to be very strong. There remains a strong need, consequently, to develop improved synthesis routes of Oseltamivir Phosphate.

SUMMARY OF THE INVENTION

The present invention provides improved methods for preparing derivatives of unsaturated, cyclic, organic acids. Preferred aspects involve esterifying, ketalizing, and incorporating leaving groups into (e.g. mesylating or tosylating) these materials. The principles of the present invention are particularly useful in synthesizing Oseltamivir Phosphate from shikimic acid or salts thereof. In particular, the present invention provides an elegant, efficient synthesis for converting shikimic acid or a salt thereof into the compound

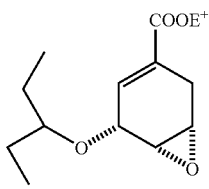

which is known as EEC-epoxide. This epoxide is an important intermediate in the synthesis of Oseltamivir Phosphate.

In one aspect, the present invention relates to a method of making an ester of an unsaturated, cyclic acid or salt thereof, comprising the step of esterifying the acid or salt thereof in the presence of an aromatic acid while removing water during at least a portion of the esterifying.

In another aspect, the present invention relates to a method of making a ketal functionalized ester of a cyclic, unsaturated acid or salt thereof, comprising the steps of:

esterifying the cyclic, unsaturated acid or salt thereof to form an ester of the acid or salt thereof, said ester comprising at least two pendant hydroxyl moieties; and reacting the ester with a stoichiometric excess of a ketal under conditions effective to ketalize the ester via a transketalization reaction involving the ketal and corresponding hydroxyl moieties of the ester.

In another aspect, the present invention relates to a method of providing a ketal functional, unsaturated, cyclic ester with a pendant mesylate moiety, comprising the steps of:

esterifying an unsaturated, cyclic acid or salt thereof to form an ester thereof, said ester comprising at least two hydroxyl moieties;

reacting the ester with a stoichiometric excess of a ketal under conditions effective to ketalize the ester via a transketalization reaction involving the ketal and corresponding hydroxyl moieties of the ester; and incorporating a leaving group into the ketalized shikimic acid ester that is capable of being displaced by an OH to form an epoxide moiety.

In another aspect, the present invention relates to a method of providing a ketal functional, shikimic acid ester with a pendant mesylate moiety, comprising the steps of:

esterifying shikimic acid or salt thereof to form a shikimic acid ester;

reacting the shikimic acid ester with a stoichiometric excess of a ketal under conditions effective to ketalize the shikimic acid ester to form a ketalized shikimic acid ester; and incorporating a leaving group into the ketalized shikimic acid ester.

In another aspect, the present invention relates to a method of providing an epoxide functional, ketalized, shikimic acid ester, comprising the steps of:

esterifying shikimic acid to form a shikimic acid ester;

reacting the shikimic acid ester with a stoichiometric excess of a ketal under conditions effective to ketalize the shikimic acid ester to form a ketalized shikimic acid ester; and incorporating a leaving group into the ketalized shikimic acid ester;

subjecting the ketalized shikimic acid ester to a ketal ring opening reaction to provide a shikimic acid ester having adjacent hydroxyl and leaving group functionality; and converting the adjacent hydroxyl and leaving group functionality to an epoxide moiety.

In another aspect, the present invention relates to a method of providing an epoxide functional, ketalized, shikimic acid ester, comprising the steps of:

esterifying shikimic acid to form a shikimic acid ester;

reacting the shikimic acid ester with a stoichiometric excess of a ketal under conditions effective to ketalize the shikimic acid ester to form a ketalized shikimic acid ester; and mesylating the ketalized shikimic acid ester;

subjecting the ketalized shikimic acid ester to a ketal ring opening reaction to provide a shikimic acid ester having adjacent hydroxyl and mesylate functionality; and converting the adjacent hydroxyl and mesylate functionality to an epoxide moiety.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention. All patents, published applications, other publications, and pending patent applications, if any, are incorporated herein by reference in their respective entireties for all purposes.

A first aspect of the present invention relates to esterifying an unsaturated, cyclic organic carboxylic acid or salt thereof. If one or more salts are used, it often is desirable to convert this to free acid in situ or otherwise to avoid neutralizing an acid catalyst used in esterification reactions using such catalysts. The first aspect of the present invention is especially applicable to unsaturated, cyclic organic acids or salts thereof comprising not only carboxylic acid functionality but also comprising one or more pending hydroxyl moieties. These acids may include one or more cyclic moieties, which may be fused, non-fused, bridged, or the like. A representative class of unsaturated, cyclic organic acids and salts thereof has the following formula:

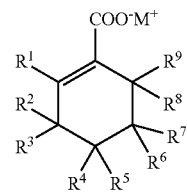

wherein each of $R^1$ through $R^9$ is independently a monovalent moiety such as hydrogen; linear, branched, or cyclic alkyl; hydroxyl or a hydroxyl-containing moiety; aryl; combinations of these, and the like; and M is selected from H and a monovalent cation such as $Na^+$, $K^+$, $NH_4^+$, $Li^+$, combinations of these and the like. Preferably $M^+$ is hydrogen, and at least one of the $R^1$ through $R^9$ groups is hydroxyl with the remaining groups being hydrogen, aryl, or alkyl. More preferably, at least two, more preferably at least 3 of the $R^1$ through $R^9$ substituents on adjacent carbon atoms comprise a hydroxyl moiety.

A preferred example of such an organic acid or salt thereof is shikimic acid or its salts. Shikimic acid can be esterified, ketalized, mesylated, and then epoxidized to prepare important precursors in the synthesis of the anti-influenza drug Oseltamivir Phosphate.

Shikimic acid is commercially available with purity assays typically ranging from 85% to 99%. Shikimic acid having a purity assay of at least about 97% is preferred, especially when being used to synthesize precursors of Oseltamivir Phosphate. Using such higher purity shikimic acid allows the acid to be used in multistep reaction schemes in which intermediates need not be isolated before being used in subsequent reaction steps. Shikimic acid, which from one perspective may be viewed as a cyclic acrylic acid, and its salts have the following formula:

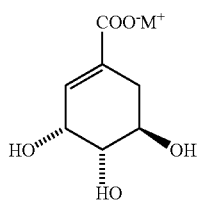

wherein $M^+$ is selected from H and a monovalent cation such as $Na^+$, $K^+$, $NH_4^+$, $Li^+$, combinations of these and the like. The ester form of this acid has the following formula:

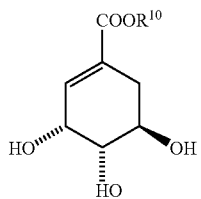

wherein $R^{10}$ is a linear, branched, or cyclic alkyl moiety. Preferably, $R^{10}$ is an alkyl moiety including 1 to 5 carbon atoms, especially ethyl.

The esterification reaction generally occurs by reacting the unsaturated, cyclic, organic carboxylic acid and/or salt thereof with a suitable co-reactant that is a source of the alkyl moiety, e.g., the $R^{10}$ moiety in the case of shikimic acid ester, forming part of the ester functionality. Suitable co-reactants include corresponding alcohols such as methanol, ethanol, isopropyl alcohol, i-butanol, n-butanol, and the like. Alcohols such as ethanol and isopropyl alcohol are preferred as these can also readily function as at least a portion of the solvent in which the esterification reaction is carried out. An advantage of using alcohols is that these are compatible with a transketalization reaction, which optionally may be carried out as a next step following esterification. As a consequence of this compatibility, the alcohol need not be removed and the subsequent transketalization may be carried out without having to isolate the esterified material.

In representative embodiments using liquid alcohol as a co-reactant/solvent, using from about 10 mmoles to 10,000 mmoles, preferably 50 to 1000 mmoles of the acid per 100 to 10000 ml, preferably 200 to 500 ml of alcohol would be suitable. When the co-reactant is also at least part of the solvent, the co-reactant is present in substantial stoichiometric excess. This helps the reaction proceed to completion.

The esterification reaction may be carried out at a wide range of temperatures. Suitable temperatures may range from just above the freezing temperature of the reaction medium to the reflux temperature of the medium. Because the reaction occurs faster at hotter temperatures, the reaction desirably occurs at reflux, which is pressure dependent. At higher pressures, the reflux temperature tends to be higher. It is often desirable to carry out the reaction at reflux under ambient conditions or even a vacuum so that reflux does not occur at too high a temperature. At higher temperatures, greater amounts of by-products may form. For instance, a reactant such as shikimic acid can have a greater tendency to form an ester dimer with itself or to undergo transesterification at higher temperatures. For the same reasons, in those embodiments in which it is further desirable to remove constituents of the reaction medium, this removal occurs under vacuum.

The esterification reaction is preferably a Fischer esterification occurring in the presence of an acid catalyst sufficiently strong to help catalyze the reaction. It is further desirable that the acid functionality of the acid catalyst is a moiety other than carboxylic acid functionality and that the acid functionality of the catalyst that is less reactive with the esterification reagent as compared to carboxylic acid. Conventionally, thionyl chloride has been used to carry out esterification of organic acids such as shikimic acid. Thionyl chloride, though, is relatively toxic and requires extra precautions and reactors for its use and for the gases that evolve during its use. To avoid the handling concerns of using thionyl chloride, the present invention preferably carries out the Fischer esterification in the presence of an aromatic, organic acid other than a carboxylic acid, especially aromatic sulfonic acids such as benzenesulfonic acid (BSA) or p-toluenesulfonic acid (PTSA). Sulfonic acids do form esters to some degree, but the formation of sulfonic acid ester is a much slower reaction than esterification of a carboxylic acid. In practical effect, the sulfonic acid catalyst cannot compete effectively with the unsaturated, cyclic, organic carboxylic acid. The PTSA is often supplied in the form of a hydrate, such as a monohydrate. Because the esterification reaction and/or subsequent reactions are generally carried out as anhydrously as possible, BSA is more preferred.

The amount of the acid catalyst used may vary over a wide range. As suggested guidelines, using from about 0.5 to about 40 mol percent, preferably 5 to about 25 mol percent of the acid catalyst would be suitable. Lesser amounts of acid catalyst could be used, but the reaction may proceed slower than might be desired. Greater amounts of acid catalyst could be used, but this gets more expensive. Generally, using a greater amount of the acid catalyst causes the reaction to proceed faster. For example, the esterification reached equilibrium after about 16 hours at reflux when using 5 mole percent, or after about 10 hours using 10 mole percent, or after about 5 hours using about 20 mole percent BSA to catalyze the esterification of shikimic acid with ethanol at reflux temperature. The mol percent of acid catalyst is given by the expression $(C/A) \times 100$ percent, wherein C is the mols of acid catalyst and A is the mols of unsaturated, cyclic organic carboxylic acid or salt thereof. Using about 10 mol % of acid catalyst is presently preferred.

As alternatives to using sulfonic acids such as BSA or PTSA, other classes of acid catalyst materials may be used. These include acid functional ion exchange resins such as the ion exchange resin available under the trade designation Amberlyst 15 from GFS Chemicals, Inc. This resin is a polystyrene including pendant sulfonic acid functionality. The reaction may take longer, e.g., a week, to reach equilibrium when using such a resin. Inorganic acids such as sulfuric acid may also be used, although the reaction may proceed more slowly than might be desired.

When using an extremely strong anhydrous acid such as thionyl chloride as an acid catalyst, equilibrium is reached when a relatively high amount of the shikimic acid is converted to the ester. However, when using alternative acids such as BSA or PTSA, equilibrium tends to be reached when only about 95% to about 96% of the carboxylic acid is converted to ester. The reaction will not progress further without removing the by-product water. Some water may also be present as a constituent of the ingredients used to form the reaction medium. Accordingly, it is preferred to remove water from the reaction medium during at least a portion of the esterification in order drive the reaction closer to completion. When removing water in this way, conversions of 99.5% or more may be realized. Because water can affect the equilibrium by decreasing the yield of the desired product, it is desirable that ingredients used to form the reaction medium be supplied in as anhydrous a condition as is practical.

Water may be removed from the reaction medium in a variety of ways. According to one approach, distillation may be used to remove the water. Water can be distilled, for instance, by adding an additional organic reagent such as toluene and/or heptane to the medium. The water, ethanol, and either toluene and/or heptane tend to form a ternary azeotrope. Water is removed by distilling the azeotrope. During the course of distillation, toluene and/or heptane on the one hand, and ethanol on the other hand, may be added back until the reaction is complete.

As an alternative to distillation, water can also be removed chemically such as by reacting the water with a water scavenger such as triethyl orthoformate. When using triethyl orthoformate to scavenge water, the product is ethyl formate. The presence of the ethyl formate lowers the boiling point of the reaction medium, but otherwise seems to have no other effect upon the reaction. The triethyl orthoformate may be added at any time during the course of the esterification. In a representative scheme, the triethyl orthoformate is added after the reaction approaches or reaches equilibrium at reflux, e.g., after about 5 hours at reflux. Adding about one equivalent of the orthoformate for each equivalent of water present, or that will be present (e.g., as a by-product), would be suitable. After adding the orthoformate, heating the reaction medium at reflux is continued, e.g., for another 5 hours, as the water is scavenged and the reaction proceeds to completion.

After esterification, a variety of options are available. The ester product may be isolated, or transferred to a different solvent. Alternatively, the reaction medium containing the ester product may be concentrated or used as is for packaging, carrying out one or more additional reaction steps, or other desired handling. As just one example of a use of the ester, the ester can be ketalized to form a ketalized precursor useful in the synthesis of Oseltamivir Phosphate.

Thus, a second aspect of the present invention relates to ketalizing the ester of an unsaturated, cyclic organic acid. Such ester may be ketalized if it includes a keto moiety, appropriate hydroxyl functionality, or other appropriate functionality. The ketalized character means that the molecule incorporates a ketal moiety, e.g., as a portion of the backbone or as part of a substituent that is pendant from the backbone. A ketal moiety is a functional group including a carbon atom bonded to both —$OZ^1$ and —$OZ^2$ groups, wherein each of $Z^1$ and $Z^2$ independently may be a wide variety of monovalent moieties or co-members of a ring structure. A ketal is structurally equivalent to an acetal, and sometimes the terms are used interchangeably. In some uses, a difference between an acetal and a ketal derives from the reaction that created the group. For purposes of the present invention, though, the term ketal refers to a molecule having the resultant ketal/acetal structure regardless of the reaction used to form the group.

Representative unsaturated, cyclic, organic acid esters having a ketal group may be represented by the following general formulae:

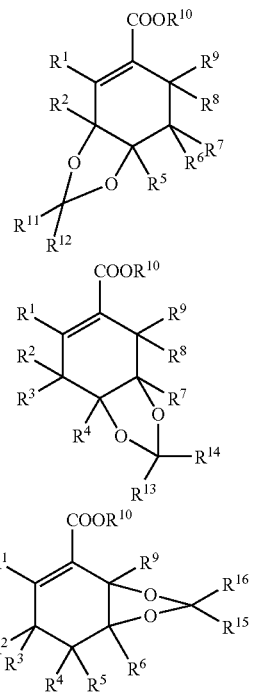

wherein each of $R^1$ through $R^{10}$ is as defined above, and each of $R^{11}$ through $R^{16}$ is independently a linear, branched or cyclic alkyl, combinations of these, and the like. The $R^{11}$ through $R^{16}$ groups on the same molecule may also be co-members of a ring structure.

Transketalization schemas are preferred over direct ketalization schema for incorporating ketal functionality into the acid ester. Direct ketalization generally involves the reaction of a keto moiety with excess alcohol as shown by the following illustrative reaction scheme in which an ester of an unsaturated, cyclic organic acid further incorporating di-hydroxyl functionality reacts with excess ketone:

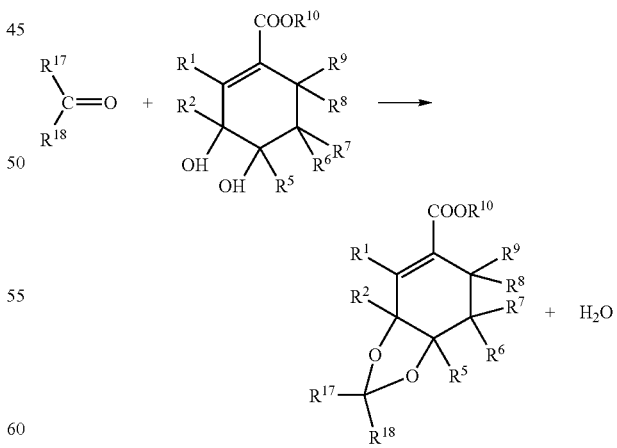

wherein $R^1$, $R^2$ and $R^5$ through $R^{10}$ are as defined above; and each of $R^{17}$ and $R^{18}$ is independently selected from linear, branched or cyclic alkyl; combinations of these and the like. The $R^{17}$ through $R^{18}$ groups on the same molecule may also be co-members of a ring structure.

For purposes of illustration, the hydroxyl groups are shown at the beta and gamma carbons relative to the carboxylate ester moiety, but these also could be pendant from any other pairs of unsaturated carbon atoms of the cyclic backbone as well. This direct ketalization reaction, however, liberates water, which is a poor leaving group in these circumstances. The water in presence of an acid can also cause the ketal to revert back to the ketone and a diol or otherwise degrade the desired product.

In contrast, in transketalization a ketone reactant is already in the form of the ketal (e.g., as dimethoxy or ethoxy in many circumstances) when reacted with hydroxyl functionality. In the context of the present invention, an illustrative transketalization reaction occurs when an ester of an unsaturated, cyclic organic acid further incorporating at least two suitable hydroxyl moieties moiety reacts with a ketal reactant as shown by the following reaction scheme:

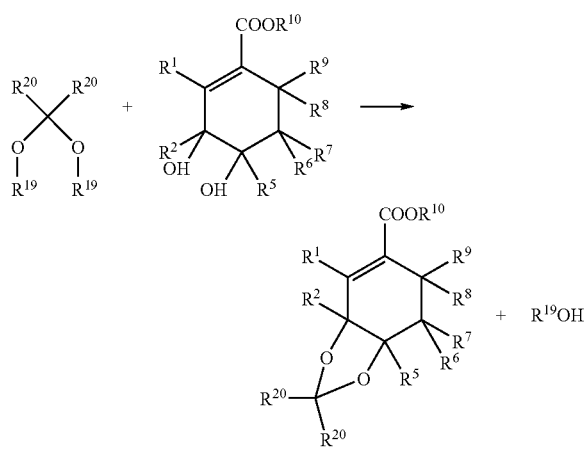

wherein $R^1$, $R^2$ and $R^5$ through $R^{10}$ are as defined above; and each $R^{19}$ and $R^{20}$ is independently selected from linear, branched or cyclic alkyl; combinations of these and the like. Each $R^{20}$ could be co-members of same ring. Preferably each $R^{20}$ is the same and each $R^{19}$ is the same. For purposes of illustration, the hydroxyl groups are shown at the beta and gamma carbons relative to the carboxylate ester moiety, but these could be pendant from any other pairs of unsaturated carbon atoms of the cyclic backbone as well.

Instead of water being the leaving group as is the case with direct ketalization, the respective alcohol(s) constitute the leaving group(s) in these kinds of transketalization reactions. The alcohol tends to be a better leaving group than water, allowing the reaction to proceed favorably and quickly to completion. As another advantage of transketalization, the alcohol generally does not function very well to revert the ketal product back to the ketal reactant. Thus, the ketal product is more stable in the reaction medium. The transketalization equilibrium strongly favors the desired product.

As still yet another advantage, transketalization allows the use of less ketal co-reactant. For instance, the 1999 Federspiel article cited herein describes using 25 eq of 3-pentanone per equivalent of the shikimic acid ester to carry out a direct ketalization of a shikimic acid ester. In contrast, a much more modest excess of the diethoxy ketal of 3-pentanone, e.g., only about a 5% to about 20% molar excess in many embodiments, is needed to carry out transketalization of the shikimic acid ester to yield the same ketalized product.

The transketalization also avoids the need to use a protecting group exchange, such as that used through the acetonide route described in the 1999 Federspiel article cited herein. The acetonide, as one drawback, has to be isolated as an intermediate clean up point. Thus, transketalization provides a more direct synthesis route and avoids an isolation associated with acetonide.

In a transketalization reaction of the present invention, the reactants may be present in their stoichiometric amounts or one of the reactants may be present in moderate excess. It is preferred, though, that the ketal reactant(s) be present in excess, as this allows the reaction to proceed more consistently to completion without requiring the addition of additional triethyl orthoformate. Using a 2% to about 50%, preferably 5% to about 30 percent excess of the ketal(s) is preferred. Using less than this may unduly impair consistency. Using more than this is an option, but is wasteful. In the case of reacting a shikimic acid ester with the pre-formed ketal 3,3-diethoxypentane, adding a small amount of additional triethyl orthoformate or the like helps to drive the reaction to completion.

In one transketalization approach, the ketal co-reactant may be pre-formed before being incorporated into the reaction medium. For instance, the ketal 3,3-diethoxypentane may be used in this reaction, being pre-formed prior to being added to the reaction pot. The 3,3-diethoxypentane can be pre-formed such as by treating 3-pentanone with triethyl orthoformate in ethanol in the presence of a catalytic amount of BSA at 25° C. for two hours. As an alternative to pre-forming the ketal co-reactant, the ketal may be formed in situ from suitable precursor(s). For instance, the ketal 3,3-diethoxypentane may be formed in situ in the reaction pot by adding appropriate amounts of triethyl orthoformate and 3-pentanone to the pot containing the ester with the remaining BSA catalyst and solvent left from the prior esterification. When forming the ketal in situ, it is preferred to use a stoichiometric excess of the triethyl orthoformate and 3-pentanone relative to the hydroxyl functional shikimic acid ester. It also is preferred to use a stoichiometric excess of the triethyl orthoformate relative to the 3-pentanone. More preferred embodiments use a 2% to 70%, preferably al 5% excess of 3-pentanone and from about 2 to about 50%, preferably a 20% excess of triethyl orthoformate.

Like the esterification reaction described above, the ketalization reaction generally occurs in the presence of an acid catalyst. The acid catalyst used for ketalization may be independently selected from the same kinds of acid catalysts suitable for esterification and used in the same amounts relative to the shikimic acid-based material. Acid catalysts such as BSA and PTSA are preferred. BSA is more preferred, inasmuch as the pre-forming or in situ forming of the ketal co-reactant desirably occurs in the absence of water, and PTSA is typically in the form of a hydrate, e.g., a monohydrate. However, when the ketal co-reactant is formed in situ as described below (e.g., 3,3-diethoxypentane is formed in situ from 3-pentanone and triethyl orthoformate), the PTSA performs reasonably comparably to BSA as an acid catalyst. It is believed that the PTSA hydrate is suitable in the in situ circumstance because the excess triethyl orthoformate reactant helps to scavenge the water from the PTSA hydrate. Also, if ketalization follows esterification according to the methodology described herein, the PTSA will have been dehydrated during esterification.

In ketalization, in contrast to the esterification reaction, much less of the acid catalyst is required. For instance, using 0.5 mol % of acid catalyst would be suitable for ketalization. However, using excess acid catalyst does not unduly affect the reaction or subsequent action taken with respect to the ketalized product. So, when more acid catalyst is already present in the ketalization reaction medium because of using the same pot as was used for esterification, the greater amount of acid catalyst present from esterification is already in the pot, so it is convenient to use that without adding more or removing some. Of course, one could add more or remove some of the acid catalyst if desired. The ketalization may occur in any suitable reaction solvent such as an alcohol, or another relatively polar nonaqueous solvent such as, e.g., DMF (N,N-dimethylformamide), an ether, a halogenated hydrocarbon, combinations of these, and the like. A reaction solvent comprising anhydrous ethanol is preferred. The concentrations of the reactants in the reaction medium may vary over a wide range. If the concentrations are too high, degradation of reactants and/or the reaction product could occur. The reaction will proceed adequately even in very dilute solutions, although using too much solvent can be wasteful. Balancing such concerns, using from 200 to 300 mmoles, preferably 287 mmoles, of the hydroxyl functional reactant per 100 to 200 ml, preferably 150 ml, of solvent would be suitable.

The transketalization reaction may occur at a wide range of temperatures over a wide range of time periods. Temperatures in the range from about room temperature up to about reflux may be used, although ambient (e.g., about 25° C.) or chilled conditions (as low as a few degrees centigrade) are preferred. Reaction times may be from a few seconds to 48 hours, preferably ten minutes to about 15 hours, more preferably about 2 hours. In one set of conditions, the reaction of 3,3-diethoxypentane with a shikimic acid ester was complete after 2 hours at 25° C. in the presence of BSA catalyst.

The transketalization of the shikimic acid ester is regioselective, because ketalizing via the two hydroxyls in a cis-orientation, e.g., on the same face of the ring, is strongly favored. The third hydroxyl, being in a trans relationship to the other two hydroxyls, is out of position to from the cyclic ketal structure as readily. In other words, the 4,4 ketalization is favored since it generates a cis fused bicycle rather than the trans fusion.

In preferred embodiments, the ester prepared according to the esterification reaction described herein is transketalized according to the present invention. After the ester is formed above, it typically is in admixture with other constituents of the reaction medium and products thereof, and at this stage typically includes not only ester, but also a solvent such as ethanol and an acid catalysts such as BSA, PTSA, or the like. This pot may be carried forward to the ketalization reaction in a variety of ways. According to one approach, the ester can be isolated first prior to being ketalized. Alternatively, the ketalization advantageously occurs without isolation of the ester. In those embodiments, the ketalization may occur in the same pot as the esterification. This is efficient and convenient inasmuch as additional reagents, isolation, or the like, other than the ketal co-reactant or ketal precursors, are not required. The reagent in the pot provides a suitable solvent medium for ketalization, and the pot already includes the desired reactant (the ester product of esterification) and acid catalyst (e.g., BSA, PTSA, or the like as the case may be). The ketal reactant or its precursor(s) are added to the pot, and the reaction is allowed to proceed, perhaps with the further addition of triethyl orthoformate to help the reaction go to completion.

Optionally, excess solvent in the esterifying reaction medium may be removed using a suitable technique, such as vacuum distillation, prior to ketalization. However, when ketalization is carried out with the concentrated solution at atmospheric pressure, degradation of the ester and/or ketalized product may tend to occur. It is preferred then to carry out ketalization without removing the excess ethanol. In particular, a transketalization reaction is so fast that there is no adverse, practical impact upon the kinetics even when using a dilute solution. Thus, when the esterification is complete, the contents of the esterification reaction pot preferably are desirably cooled and the ketalization performed therein at ambient temperature.

After ketalization, a variety of options are available. The ketalized ester product may be isolated, transferred to a different solvent, and/or used in one or more additional reactions. Additionally or alternatively, the reaction medium containing the ketalized ester product may be concentrated or used as is for packaging, carrying out one or more additional reaction steps, or other desired handling. As just one example of a use of the ketalized ester, and in the case of the ketalized shikimic acid ester, the remaining hydroxyl of the ester can be converted to a suitable leaving group that can be displaced by an adjacent OH (which is provided when the ketal moiety is ring-opened as described below) to form an epoxide moiety. Examples of suitable leaving groups include mesylates, tosylates, combinations of these, and the like. Preferably, the ester is mesylated to form a mesylated precursor useful in the synthesis of Oseltamivir Phosphate.

When the ketalized ester product is to be mesylated, it is desirable to remove or neutralize the acid catalyst and to transfer the ketalized ester product into a more suitable mesylating solvent such as isopropyl acetate or the like. For example, an acid catalyst such as BSA, PTSA or the like can be neutralized with a base such as triethylamine. The ketalizing solvent, e.g., ethanol is some embodiments, can be removed by vacuum distillation and replaced with the desired mesylating solvent. The neutralized acid can be readily removed, such as by aqueous work up, following the mesylation reaction. Thus, another aspect of the invention relates to mesylating the ketalized, ester of an unsaturated, cyclic organic acid or salt, thereof, wherein the ketalized reactant to be mesylated includes a suitable co-reactive functionality for carrying out mesylation. Examples of complementary functionality that facilitate mesylation include, for example, hydroxyl, combinations of these and the like. Examples of mesylating agents include methane sulfonyl halides, combinations of these, and the like. Methane sulfonyl chloride is preferred.

The reactants may be present in their stoichiometric amounts or one or the other may be present in excess. Preferably, the mesylating agent is present in a suitable excess to help the mesylation of the ketalized ester proceed to completion. Generally, using a 10% to 30% 17% is preferred molar excess of the mesylating agent would be suitable.

The mesylation reaction desirably occurs at cooler temperatures to prevent loss of the ketal group, which at this stage of synthesis is protecting the other two OH groups in the case of the ketalized shikimic acid ester. Later, ring opening of the ketal provides an OH that can displace the leaving group, e.g., the mesylate group, to from an epoxide. The reaction temperature desirably is less than about 0° C., and more preferably is less than about −10° C. Accordingly, the reaction desirably occurs in a suitable solvent that allows the reaction to occur at these low temperatures. Examples of suitable solvents include one or more alkyl acetates such as isopropyl acetate, ethyl acetate, combinations of these, and the like. The isopropyl acetate is preferred, because it facilitates the extractive removal of by-products to a greater degree, thereby avoiding a solids isolation that might otherwise be required.

The concentration of reactants in the solvent may vary over a wide range. If too concentrated, the yield and purity may suffer. It may also be more difficult to stir the admixture. On the other hand, using too much solvent is wasteful. Balancing these concerns, representative mesylation reactions involve using from 200 to 300 mmol, preferably 287 mmol, of the ketalized, hydroxyl functional, unsaturated ester per 125 to 300, preferably 150 ml of solvent.

The mesylation reaction generally occurs in the presence of a suitable organic, substantially anhydrous base. A moderate excess of the base is generally used in accordance with conventional practices in order to react with the side product HCl. The base and acid react to form a water-soluble hydrochloride salt that is insoluble in the solvent, thereby removing the side product via precipitation. Examples of suitable bases include tertiary amines such as triethylamine, DEIA (diethylisopropylamine), combinations of these, and the like. Tertiary amines such as these are preferred so that the base is non-nucleophilic. Otherwise, nucleophilic bases could have a tendency to displace mesylate, tosylate, or other desired functionality that is being formed. Inorganic bases, such as carbonate and the like could also be used. Triethylamine is preferred.

The rate at which the base is added to the reaction medium can impact yield in purity. Generally, slower addition of base provides better yield and purity. But if the rate of addition is too slow, the process duration may not be as economically practical as might be desired. Balancing these concerns, it is desirable to add the base over time periods ranging from at least 10 minutes to 48 hours, preferably 2 hours to about 20 hours, more preferably about 5 hours.

As an alternative to adding the base slowly, at least a portion of the base may be present initially while one or more of the other constituents is slowly added. For instance, base can be charged to a solution of the ketal in solvent, while the mesylating agent is slowly added over time according to the time ranges recited above for slow base addition. Alternatively, the solution may initially contain ketal in solvent, while both the base and mesylating agent are slowly added according to the time ranges recited above for slow base addition.

A specific example of a mesylation according to the present invention is a reaction in which a ketalized shikimic acid ester is mesylated using methane sulfonyl chloride as the mesylating agent in isopropyl acetate using triethylamine as the base. This reaction conveniently occurs at a temperature of –10° C. or less. The mesylating agent is added to the solution containing the ketal in isopropyl acetate, while the base is slowly added using a syringe pump over a period of 5 hours. When the mesylation reaction is complete, the solution can be warmed, e.g., to about 0° C. Water is added to wash the organic layer containing the desired product one or more times. The organic and aqueous layers may invert with the first or subsequent water washes. To help prevent this from happening, more isopropyl acetate can be added.

The following illustrates how the principles of the present invention may be used to convert shikimic acid to the epoxide functional shikimic acid ester derivative known as EEC epoxide, an important precursor in the synthesis of Oseltamivir Phosphate. The synthesis is shown by the following reaction scheme:

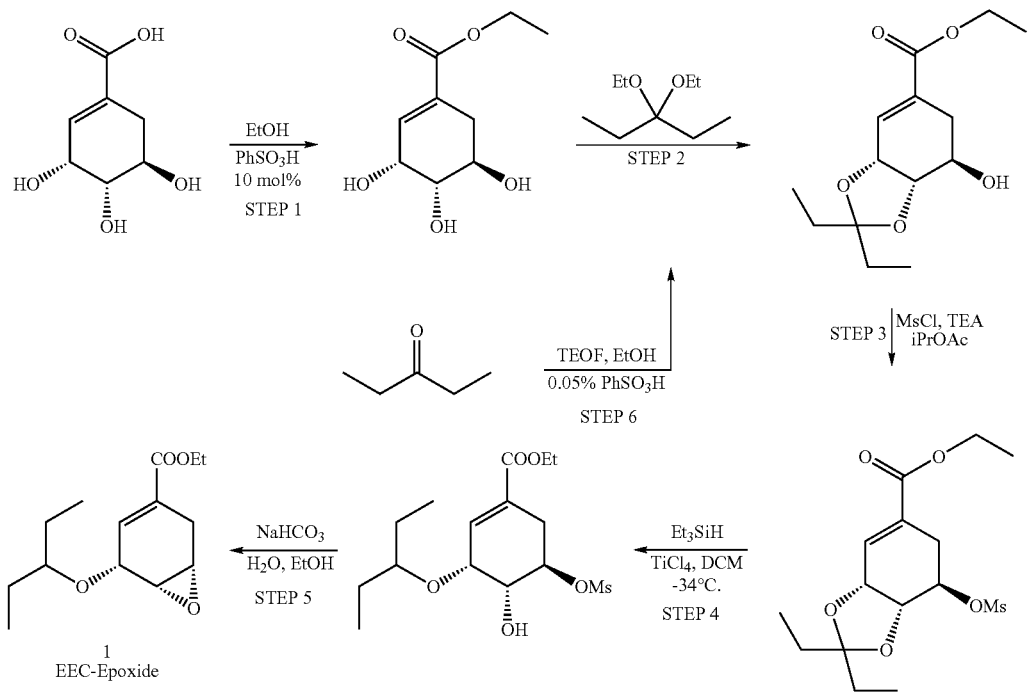

As an overview of the synthesis, a Fischer esterification of shikimic acid is carried out in ethanol in the presence of benzene sulfonic acid. Removing water during at least a portion of the esterification obviates the need for special care and equipment that otherwise might be required if thionyl chloride were to be used. Shikimic acid is an excellent starting material in the synthesis of the epoxide as compared to quinic acid inasmuch as shikimic acid already includes the desired unsaturation (double bond) in the correct position. This process preferably uses shikimic acid that has a purity of 97.5% or better. The direct transketalization of this ester occurs in the same reaction vessel. Triethyl orthoformate and 3-pentanone are added to the pot containing the shikimic acid ester. The ketal 3,3-diethoxy pentane is formed in situ and the shikimic acid ester is transketalized. The mesylation of this product then occurs in isopropyl acetate in the presence of triethylamine to provide the mesylated, ketalized shikimic acid ester. A reductive ring-opening (cleavage) of the ketal moiety occurs. This is followed by epoxidation to provide the EEC-Epoxide precursor. The yield, the overall purity, and impurity profile of the final EEC-Epoxide made with this process are all excellent and suitable for commercial scale production.

This synthesis has many advantages. Due to the improved quality of the shikimic acid that is now commercially available, a single isolation of the final product is sufficient for providing a quality clean up via crystallization or the. The synthesis avoids the need for thionyl chloride during esterification, replacing it with a safer alternative such as benzene sulfonic acid. Direct ketalization of the shikimic acid ester with neat diethoxypentane (which may be formed in situ from suitable precursors) provides the desired ketal without going through the acetonide, which eliminates a solid isolation and crystallization associated with the acetonide synthesis route. The mesylation step is performed in isopropyl acetate, which allows for an emulsion free extraction of the triethylammonium chloride by-product. This again eliminates a solid isolation that is necessary in the conventional process. The last two steps, i.e., ring opening and epoxidation, may be conducting according to the literature, such as is described in the 1999 Federspiel article cited herein.

Further details of this synthesis and additional principles of the present invention will now be described with reference to the following illustrative examples.

EXAMPLE 1

Esterification, Ketalization, and Mesylation of Shikimic Acid

Ester Reaction

To a 500 mL jacketed 3-neck flask fitted with mechanical stirrer, reflux condenser, and thermometer, add 50 g (0.287 moles) Shikimic Acid, 150 mL SDA 2B-3 ethanol, and 5.5 g (0.029 moles) p-Toluenesulfonic acid, monohydrate (or 5.7 g (0.029 moles) 80% Benzenesulfonic acid solution in ethanol). Using a bath set at 90-95° C., heat the slurry to reflux for five hours. Cool slightly and add 46.9 g (0.316 moles) Triethyl orthoformate (if benzenesulfonic acid was used as catalyst, use 42.6 g (0.287 moles) triethyl orthoformate). More Triethyl orthoformate is needed to react with the water of hydration when PTSA is used as catalyst. Continue heating at reflux (78 to 80° C. bath) until the Shikimic acid is 1% or less (about 5 hours).

An alternative to chemically removing the water byproduct with Triethyl orthoformate is to remove water by azeotropic distillation using Toluene. Initially 50 mL Toluene is added and distilled off. Additional charges of 35 mL Toluene and 15 mL Ethanol are used until the esterification is complete.

Ketal Reaction

Cool the solution to 25° C. and add 51.1 g (0.344 moles) Triethyl orthoformate and 28.4 g (0.330 moles) 3-Pentanone. Stir 5 minutes and sample for completion. Continue stirring until the ester is 1% or less. (It may be necessary to add additional Triethyl orthoformate). Neutralize with about 4.8 mL Triethylamine to a pH of about 8. Using a bath temperature of 35° C., vacuum distill off ethanol to a residue and charge 150 mL Isopropyl acetate. Repeat the distillation to a residue and recharge 150 mL Isopropyl acetate. If the ethanol is more than 0.5%, repeat as necessary.

Mesylation Reaction

Cool the Isopropyl acetate solution of ketal to −5° C. or below and add 26 mL (0.336 moles) Methanesulfonyl chloride. Cool the solution to −10° C. and feed 78 mL (0.561 moles) Triethylamine via syringe pump over 5 hours keeping the temperature at −12 to −10° C. Stir 30 minutes and sample for completion. When less than 0.5% ketal remains, warm the slurry to 0° C., charge 100 mL water, stir 30 minutes, and allow the layers to settle. Separate the layers and discard the lower aqueous layer. Charge 100 mL water and 100 mL Isopropyl acetate to the organic layer, stir 30 minutes, settle and separate. Vacuum distill the organic layer using a 35° C. bath and replace Isopropyl acetate with 70 mL Dichloromethane until the Isopropyl acetate is 0.5% or less. End with a solution of mesylate in 70 mL Dichloromethane.

EXAMPLE 2

Fischer Esterification of (−)-Shikimic Acid

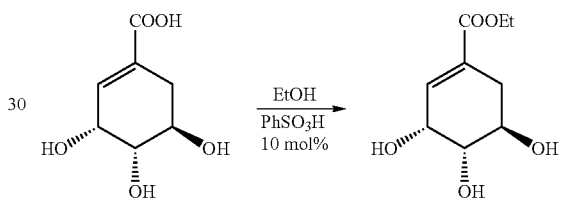

In a 500 ml round bottomed flask equipped with a thermocouple, mechanical stirrer, condenser and inert gas supply was added 100 g of Shikimic Acid (574.2 mmoles) followed by the addition of 9.18 g Benzene Sulfonic Acid (28.7 mmoles, 5 mole %, but note that 10 mol % may be used). 300 ml Ethanol (2B-3) was added and the slurry was heated to reflux (bath temperature set at 90° C. and head temperature holds steady −75° C.).

The reaction was followed by GC analysis. When the amount of shikimic acid was <3%, the solvent was stripped (~75%, ~225 ml removed) and taken on crude to the next step as described in Example 3. The reaction time was approx. 12 h.

The procedure of this example may also be carried out using 25 mole % of the benzene sulfonic acid, in which case the reaction time was decreased to 5 h.

EXAMPLE 3

Ketalization

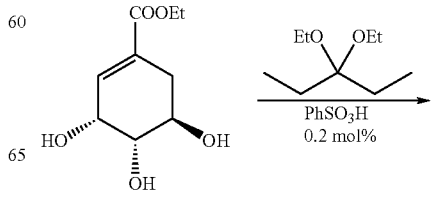

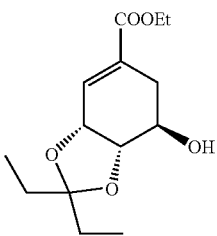

In a 250 ml round bottomed flask equipped with a magnetic stirrer, and inert gas supply was added 96 ml Triethylorthoformate (574 mmoles) followed by the addition of 61 ml 3-Pentanone (574 mmoles) and 34 ml Ethanol (574 mmoles) and 182 mg Benzene Sulfonic acid (0.2 mol %, 1.15 mmol). The reaction was stirred at room temperature for a minimum of 3 h. This solution was transferred to the shikimic acid ethyl ester mixture from the previous step and stirred at room temperature for an additional 2 h. To the vessel was charged 300 ml Isopropyl Acetate and 100 ml City water. This mixture was stirred for 15 min and the layers were separated. 100 ml saturated NaHCO$_3$ was charged, stirred for 15 min and separated. 100 ml City water was charged, stirred for 15 min and separated. The combined aqueous layers were back extracted with 300 ml Isopropyl acetate and the solvent was stripped in vacuo (40° C., 200 mmHg-25 mmHg) to afford an oil that solidified upon standing. (152 g, 98.2%).

Analytical Data for the Ethyl 3,4-O-Isopentylidene Shikimate product was as follows:

$^1$H NMR (500 MHz, CDCl$_3$) δ0.89 (t, J=7.5 Hz, 3H), 0.93 (t, J=7.5 Hz, 3H), 1.30 (t, J=7.0 Hz, 3H), 1.67 (m, 4H), 2.28 (br. m, 1H) 2.79 (dd, J=17.0, 4.5 Hz, 2H), 3.92 (m, 1H), 4.12 (q, J=7.0 Hz, 2H), 4.23 (dd, J=14.0, 7.0 Hz, 1H), 4.77 (m, 1H), 6.93 (m, 1H); $^{13}$C NMR (125 MHz, CDCl$_3$) δ8.14, 8.78, 14.39, 29.36, 29.54, 29.91, 61.28, 69.17, 72.47, 78.08, 113.87, 130.65, 134.27, 166.40; IR (neat) 3285, 2981, 2942, 1702, 1276, 1108 cm$^{-1}$; HRFABMS found m/z: 293.152 (M+Na$^+$), calcd. for C$_{14}$H$_{22}$O$_5$Na (293.136).

EXAMPLE 4

Mesylation of Ketal

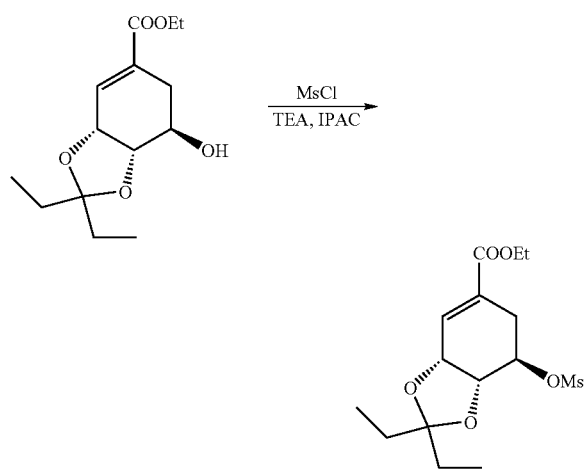

In a 21 round bottomed flask equipped with a mechanical stirrer, and inert gas supply and charged with 152 g hydroxy ketal (564 mmol) from the previous step was added 600 ml Isopropyl Acetate (17 mole equivalents/3.4 wt. eq.) and the solution was cooled to 0° C. 10 ml Mesyl Chloride (733 mmoles, 1.3 equiv) was added followed by the slow addition of 173 ml Triethylamine (2.2 equiv. 1.24 mole) through a dropping funnel. This addition is very exothermic and the addition rate was maintained such that the reaction temperature never exceeded 10° C. A voluminous precipitation occurred during the addition and once the triethylamine addition was complete, the reaction was stirred for an additional 30 min. The reaction was followed by HPLC and once the starting material was <3%, the reaction was quenched by the addition of 300 ml City water. This mixture was stirred for 15 min after which time the layers were separated and another charge of 300 ml City water was added, stirred for 15 min and separated. The solvent was stripped in vacuo to afford a yellow oil (Yield based on wt. assay for step=88%; 86% over three steps).

EXAMPLE 5

Silane Reduction

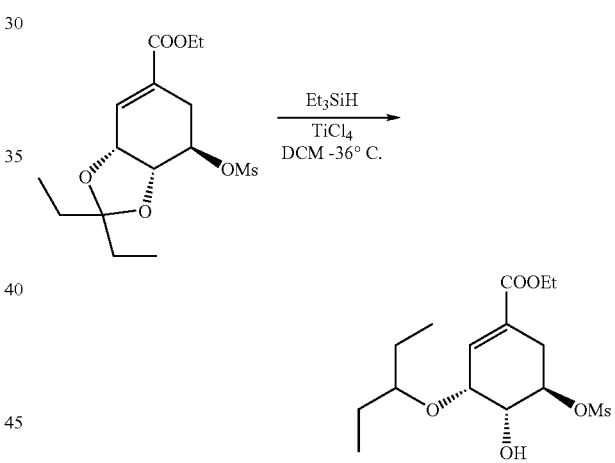

In a 500 ml round bottomed flask equipped with a magnetic stirrer, inert gas supply and charged with crude 145 g Mesylate (416 mmol) from the previous step was added 600 ml Dichloromethane (25 mole equivalents/5.5 wt. eq.) and 87 ml Triethylsilane (541 mmol, 1.3 equiv) and the solution was cooled to −36° C. A solution of 50 ml Titanium Tetrachloride (458 mmoles, 1.1 equiv) in 60 ml Dichloromethane was prepared and added slowly via addition funnel.

This addition is exothermic and the addition rate was maintained such that the reaction temperature never exceeded −32° C. (about 90 min).

When the reaction was complete, the reaction mixture was poured onto 100 ml ice/H$_2$O and the mixture was poured into a separation funnel. The organic phase was washed with 150 ml saturated NaHCO$_3$, the phases separated and the organic layer stripped under vacuum to afford a pale yellow oil which solidified upon standing. The crude mix was taken on to the next step without further purification.

EXAMPLE 6

Epoxide Formation

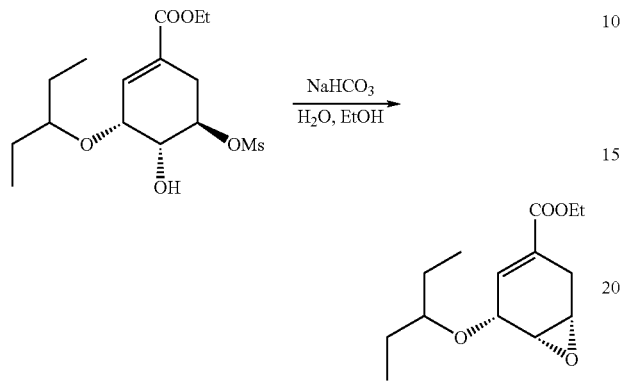

In a 2 l round bottomed flask equipped with a mechanical stirrer was charged crude 146 g Hydroxy mesylate (416 mmol) from Example 5 followed by 400 ml Ethanol (25 mole equivalents/5.5 wt. eq.) and 56 g in 750 ml 7.5% $NaHCO_3$ solution (666 mmol, 1.6 equiv) and the solution was heated to 60° C. for 2 h. The reaction mixture was cooled to 35° C. and extracted with 4×100 ml Hexane. The combined organic layers were washed once with 100 ml City water and concentrated to half volume. The pale yellow solution was cooled to −18° C. At 15° C., the product spontaneously crashed out of solution. The product was filtered and washed with cold 100 ml hexane. The epoxide product was dried and isolated as a white fluffy solid (105 g, 83% yield over last two steps and 72% overall).

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of making a ketal functionalized ester of a cyclic, unsaturated acid or salt thereof, comprising the steps of:
   a) esterifying the cyclic, unsaturated acid or salt thereof in the presence of an aromatic acid to form an ester of the acid or salt thereof, said ester comprising at least two pendant hydroxyl moieties; and
   b) reacting the ester with a stoichiometric excess of a ketal in the presence of the aromatic acid under conditions effective to ketalize the ester via a transketalization reaction involving the ketal and corresponding hydroxyl moieties of the ester, wherein the ketal is formed in situ in the presence of the ester.

2. The method of claim 1, wherein the unsaturated, cyclic acid or salt thereof comprises shikimic acid or a salt thereof.

3. The method of claim 1, wherein the aromatic acid comprises a sulfonic acid moiety.

4. The method of claim 1, wherein the aromatic acid is substantially free of carboxylate functionality.

5. The method of claim 1, wherein the aromatic acid is selected from benzene sulfonic acid or p-toluene sulfonic acid, or a hydrate of p-toluene sulfonic acid.

6. The method of claim 2, comprising reacting the shikimic acid or a salt thereof with substantially anhydrous ethanol in the presence of at least one sulfonic acid.

7. The method of claim 6, wherein the sulfonic acid is benzene sulfonic acid.

8. A method of providing a ketal functional, unsaturated, cyclic ester with a pendant mesylate moiety, comprising the steps of:
   a) esterifying an unsaturated, cyclic acid or salt thereof in the presence of an aromatic acid to form an ester thereof, said ester comprising at least two hydroxyl moieties while removing water during at least a portion of the esterifying;
   b) reacting the ester with a stoichiometric excess of a ketal under conditions effective to ketalize the ester via a transketalization reaction involving the ketal and corresponding hydroxyl moieties of the ester, wherein the ketal is formed in situ in the presence of the ester; and
   c) incorporating a leaving group into the ketalized ester that is capable of being displaced by an OH to form an epoxide moiety.

9. The method of claim 8, wherein the leaving group comprises a mesylate, a tosylate, or combinations thereof and the step of incorporating the mesylate into the ketalized ester occurs in a solvent comprising isopropyl acetate.

10. The method of claim 8, wherein the ketalizing reaction occurs without isolating the ester used as a reactant in the ketalizing reaction.

11. A method of providing a ketal functional, shikimic acid ester with a pendant mesylate moiety, comprising the steps of:
    a) esterifying shikimic acid or salt thereof to form a shikimic acid ester;
    b) reacting the shikimic acid ester with from 2% to 50% of a stoichiometric excess of a ketal under conditions effective to ketalize the shikimic acid ester to form a ketalized shikimic acid ester, wherein the ketal is formed in situ in the presence of the ester; and
    c) incorporating a leaving group into the ketalized shikimic acid ester.

12. A method of providing an epoxide functional, ketalized, shikimic acid ester, comprising the steps of:
    a) esterifying shikimic acid to form a shikimic acid ester;
    b) reacting the shikimic acid ester with from 2% to 50% of a stoichiometric excess of a ketal under conditions effective to ketalize the shikimic acid ester to form a ketalized shikimic acid ester, wherein the ketal is formed in situ in the presence of the ester; and
    c) incorporating a leaving group into the ketalized shikimic acid ester;
    d) subjecting the ketalized shikimic acid ester to a ketal ring opening reaction to provide a shikimic acid ester having adjacent hydroxyl and leaving group functionality; and
    e) converting the adjacent hydroxyl and leaving group functionality to an epoxide moiety.

13. A method of providing an epoxide functional, ketalized, shikimic acid ester, comprising the steps of:
    a) esterifying shikimic acid to form a shikimic acid ester in the presence of an aromatic acid;
    b) reacting the shikimic acid ester with from 2% to 50% of a stoichiometric excess of a ketal in the presence of the aromatic acid under conditions effective to ketalize the shikimic acid ester to form a ketalized shikimic acid ester, wherein the ketal is formed in situ in the presence of the ester; and c) mesylating the ketalized shikimic acid ester;

d) subjecting the mesylated, ketalized shikimic acid ester to a ketal ring opening reaction to provide a shikimic acid ester having adjacent hydroxyl and mesylate functionality; and e) converting the adjacent hydroxyl and mesylate functionality to an epoxide moiety.

14. A method of making a ketal functionalized ester of a cyclic, unsaturated acid or salt thereof, comprising the steps of:

a) charging a cyclic, unsaturated acid or salt thereof to a reaction vessel, the acid or the salt thereof comprising a carboxylic acid moiety and one or more pending hydroxyl moieties;

b) esterifying the acid or salt thereof in the reaction vessel to form an ester of the acid or salt thereof in the presence of an aromatic acid while removing water during at least a portion of the esterifying;

c) forming a stoichiometric excess of a ketal in situ in the reaction vessel in the presence of the ester; and d) transketalizing the ester in the reaction vessel by reacting the ester with the in situ formed ketal.

* * * * *